United States Patent [19]

Puls et al.

[11] 4,260,840
[45] Apr. 7, 1981

[54] BUTENE-1 CONTAINING FEED PURIFICATION PROCESS(CS-165)

[75] Inventors: Friedrich H. Puls, Baton Rouge, La.; Klaus D. Ruhnke, Pulheim, Fed. Rep. of Germany

[73] Assignee: Exxon Research & Engineering Co., Florham Park, N.J.

[21] Appl. No.: 111,245

[22] Filed: Jan. 11, 1980

[51] Int. Cl.$^3$ .............................................. C07C 5/03
[52] U.S. Cl. ...................................... 585/259; 585/261
[58] Field of Search ................................ 585/259, 261

[56] References Cited

U.S. PATENT DOCUMENTS

| 2,946,829 | 7/1960 | Likins | 585/260 |
|---|---|---|---|
| 2,964,579 | 12/1960 | Kirsch et al. | 585/260 |
| 3,076,858 | 2/1963 | Frevel et al. | 585/262 |
| 3,113,983 | 12/1963 | Kirsch et al. | 585/259 |
| 3,481,999 | 12/1969 | Reich | 585/259 |
| 3,485,887 | 12/1969 | Kronig et al. | 585/260 |
| 3,655,621 | 4/1972 | Kasperik et al. | 585/262 |
| 3,804,916 | 4/1974 | Lalancette | 585/261 |
| 4,078,011 | 3/1978 | Glockner et al. | 585/262 |

FOREIGN PATENT DOCUMENTS 1497627 1/1978 United Kingdom .

OTHER PUBLICATIONS

Wells, Chemistry & Industry, Oct. 17, 1964, pp. 1742-1748.
Bond et al., J. Chem. Soc. (A) 1965, pp. 3218-3227.
Fieser et al., Adv. Org. Chem., (1961) p. 181.
Peterson, "Catalysts for Hydrogenating Acetylenes" Noyes Data Corp. (1977), pp, 199-200.
Webb et al., J. Chem. Soc., (A), 1968 pp. 3064-3069.

Primary Examiner—Curtis R. Davis
Attorney, Agent, or Firm—Rebecca Yablonsky

[57] ABSTRACT

The invention concerns selectively hydrogenating butadiene to butene in a C$_4$ fraction containing at least 30 weight % butene-1 by treatment with hydrogen under carefully controlled conditions which comprise in combination use of a supported palladium catalyst containing about 0.01 to about 1.0 weight % palladium, a small excess of hydrogen over theoretical, temperatures in the range of about 50° to 90° C., pressures sufficient to maintain the hydrocarbons in a mixed vapor-liquid phase and a mass velocity of above 1500 lbs./(Sq. ft.×H).

10 Claims, 1 Drawing Figure

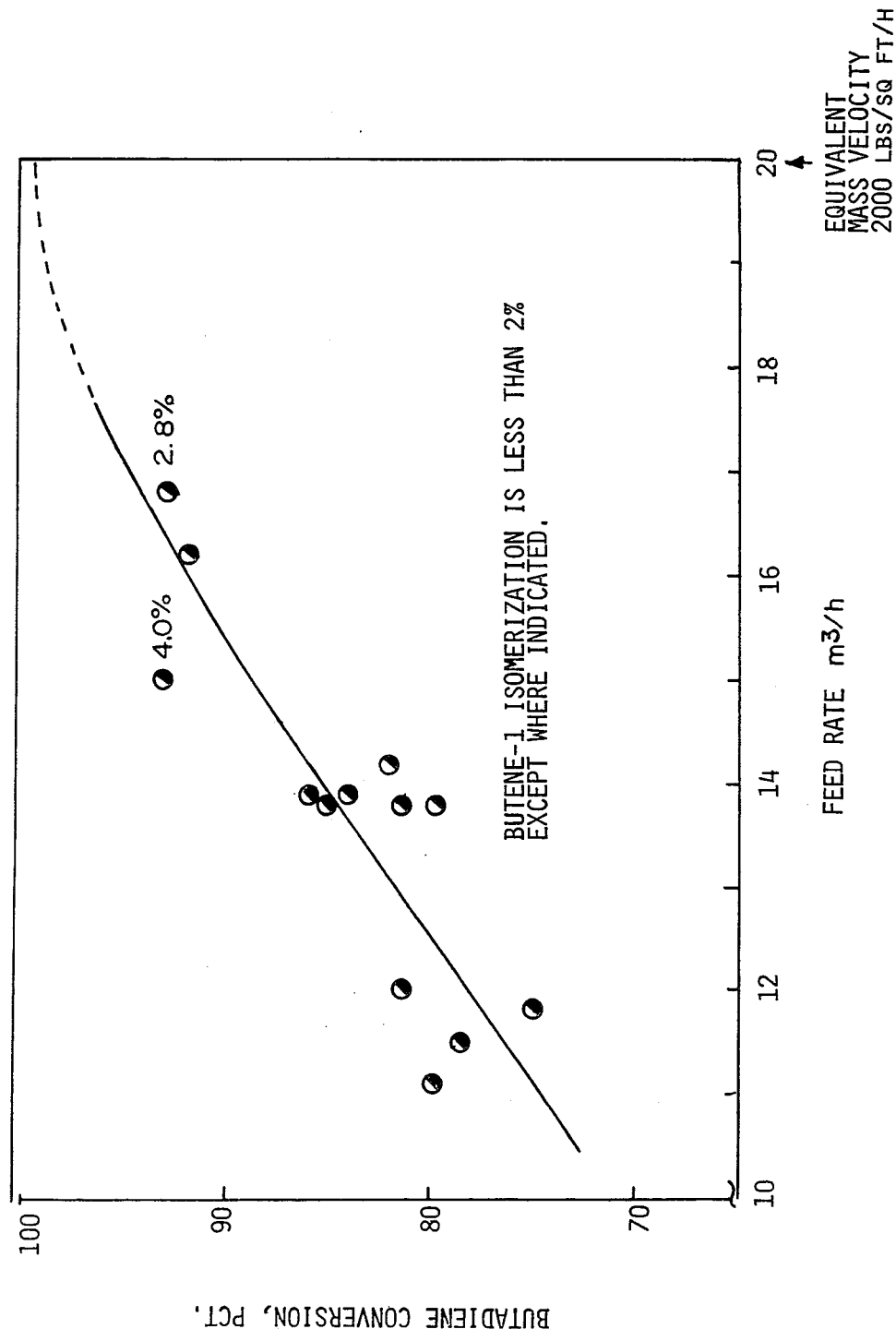

BUTENE-1 CONTAINING FEED PURIFICATION PROCESS(CS-165)

BACKGROUND OF THE INVENTION

1. Field of the Invention

This invention relates to the selective hydrogenation of butadiene contained in commercial streams containing unsaturated hydrocarbons. In particular, this invention relates to the treatment of hydrocarbon mixtures, in which butene-1 is present in a substantial amount of at least 30% and is to be preserved, with hydrogen in the presence of a solid hydrogenation catalyst, such as a palladium-containing catalyst, to convert the butadiene (1,3) to butene with avoidance of first isomerization of butene-1 to butene-2 and second hydrogenation of butene-1 and of butene-2 to butane.

The invention is also applied to the selective hydrogenation treatment of other impurities present in butenes such as acetylenes and sulfur compounds such as mercaptans and other unidentified impurities which react with hydrogen. Thus, this invention relates to a process for purifying butene-1 containing streams.

Butene-1 is of commercial interest as a modifier in the production of polyethylene and as a raw material for polybutene manufacture. Other uses include catalytic dimerization of butene-1 to octenes and 2-ethyl-hexene-1, and use as a raw material in rhodium catalyzed hydroformylation processes to produce normal pentylaldehyde. For such uses a butene-1 rich stream containing not more than 500 ppm, preferably not more than 100 ppm butadiene, is desirable as feedstock to prevent catalyst aging and byproduct polymer formation.

Butene streams obtained from cracking of hydrocarbons are treated for recovery of contained butadiene and thereafter typically contain 0.3% to 6.0% of residual butadiene which makes these cracked streams without hydrofining unsuitable as raw material for the above mentioned uses.

Since butene-1, which is an alpha olefin, is the desired starting material for the above mentioned applications rather than its non-reactive or less reactive isomers having an internal double bond, cis- and trans-butene-2, any loss of the former due to isomerization of butene-1 to butene-2 should be kept to a minimum as well as any loss due to hydrogenation to butane, during hydrofining. A useful hydrofining process would, therefore, have a threefold purpose: (1) to remove butadiene adequately by hydrogenating it to n-butene, (2) to minimize conversion of n-butene to n-butane, and (3) most importantly and most difficultly, to minimize isomerization of butene-1 to butene-2. Butene streams from steam cracking after most of the co-produced butadiene has been extracted and after isobutylene has been removed typically contain 30-75% of butene-1 and may be fractionated, if desired, to contain 75-99.5% butene-1, but such fractionation does not substantially remove the residual butadiene impurity. The hydrofining step for removal of residual butadiene can be carried out prior to or after butene-1 has been concentrated by fractionation. Isomerization of butene-1 to butene-2 occurs at high reaction rates in the presence of hydrogenation catalysts, especially at higher temperatures and higher catalyst concentrations, because butene-2 is thermodynamically more stable than butene-1; in fact, the thermodynamic equilibrium at reaction temperature is about 90% butene-2 and less than 10% butene-1.

2. Description of the Prior Art

In U.S. Pat. No. 3,485,887, assigned to Bayer, a process is described for the hydrogenation of $C_4$ fractions containing butene-1 and butadiene by contacting the same with a palladium catalyst wherein the $C_4$ hydrocarbon is allowed to trickle down in the liquid phase at an inlet temperature of 10° to 35° C. and an outlet temperature of 60° to 90° C. over the fixed bed catalyst in a hydrogen atmosphere. The data show that there is very substantial isomerization of butene-1 to butene-2 and, in fact, the claims state this to be the object.

In U.S. Pat. Nos. 3,113,983, also 3,655,621, and 4,078,011, sulfided molybdenum/cobalt and nickel catalysts and higher temperatures are used to hydrogenate butadienes in $C_4$ fractions but have the potential to introduce sulfur contamination which is a severe poison to catalysts which are used with the hydrofined butene-1 product in manufacture of modified polyethylene, octenes and oxo alcohols.

Other catalyst types have been used, viz., copper-nickel in U.S. Pat. No. 3,481,999, in which vapor phase and high temperature is used in examples, and in which it is stated that hydrogen can be a multiple of that theoretically required "for example five or tenfold molar-wise". Copper plus another metal, such as Ni, Pd, is used in U.S. Pat. No. 3,076,858; and copper chromite in U.S. Pat. No. 2,964,579, both in connection with higher temperature such as 140°–200° C. and 150°–250° F., respectively. However, large concentrations of metal on the support are required in these methods. In U.S. Pat. No. 3,478,123, a ruthenium chloride catalyst is used at temperatures ranging from ambient to 300° C. with hydrogen pressures of 1 to 100 atm. In U.S. Pat. No. 3,804,916 a catalyst of nickel, palladium or platinum intercalated in graphite is employed. U.S. Pat. No. 2,946,829 stresses deposition of the palladium at the surface of the support and passes a gas mixture of propylene over the catalyst to hydrogenate acetylenes and diolefins therein.

In British Pat. No. 1,497,627 a propylene cut which is to be hydroformylated with a rhodium-triphenylphosphine catalyst, is prehydrogenated in the vapor phase over a palladium-chromium, alumina supported catalyst. The patent is not concerned with treatment of a $C_4$ fraction containing n-butenes so that the special problem of the isomerization of butene-1 to butene-2 is not considered. Propylene is not capable of isomerization. Thus, this patent does not recognize that in a commercially sized, adiabatic reactor the inlet temperature would increase across the reactor as a result of the heat of reaction in vapor phase operation and give a much higher reactor outlet temperature, especially when isomerization reactions and unwanted hydrogenation are occurring. The use of a vapor phase in this patent is limiting the ultimately achievable selectivity.

Studies have been made of the mechanism of the platinum metals as selective hydrogenation catalysts in gas phase reactions, in which the identity of the metal chosen is stressed, see Chemistry and Industry, Oct. 17, 1964, pp. 1742–1748, and see "The Hydrogenation of Alkadienes, Part. I. The Hydrogenation of Butadiene Catalyzed by the Noble Group VIII Metals", Bond, Webb, Wells and Winterbottom, Journal Chemical Society (A) 1965, pp. 3218–3227 where it is stated, p. 3225, that the routes to each butene isomer are equally affected by changes in the availability of absorbed hydrogen.

"The Hydrogenation of Alkadienes", Part II by Webb and Bates, Journal Chemical Society (A) 1968, pp. 3064–3069 discusses selectivity differences for palladium and other noble metal catalysts but also does not recognize that process conditions rather than catalyst composition can be used to achieve selective hydrofining because the authors operated in the presence of a large excess of hydrogen.

Textbook references include "Advanced Organic Chemistry" by Fieser and Fieser, Rheinhold Publishing Co., 1961, p. 181 in which the mechanism of hydrogenation on a catalyst surface is discussed for palladium and platinum catalyst, and "Hydrogenation Catalysts" by R. J. Peterson, Noyes Data Corp. 1977, pp. 199–200. In fact, it has hitherto generally been accepted in the trade and literature that selective hydrofining of butene streams to remove diolefins, acetylenes and sulfur is accompanied by the isomerization of a significant portion of butene-1 to butene-2 in the league of at least 4 to 15%, and that adequate hydrogenation of impurities is achieved by increasing the hydrogen partial pressure until sufficient conversion of impurities is attained. This increase in hydrogen pressure, it has now been found, is detrimental as it favors butene-1 to butene-2 isomerization and butene hydrogenation.

SUMMARY OF THE INVENTION

The applicants have made studies of butadiene hydrogenation in hydrocarbon fractions containing butene-1 and have recognized that the metal content of the catalyst should be small and it must not be saturated with hydrogen because hydrogen saturation of the catalyst is responsible for isomerization; that the catalyst must be sufficiently active to catalyze butadiene hydrogenation at low temperature since higher temperature favors isomerization; that the amount of hydrogen used must be limited to a small excess over that required by theory to hydrogenate impurities, such as butadiene to butene, e.g., not more than about one mole of excess hydrogen per 100 moles of butene-1; that a high mass velocity above 1500 lbs/(sq.ft.×hr) must be used in plant scale operation to utilize fully the scarcely available hydrogen and small metal catalyst concentration; and that the butene-containing stream should be at its bubble point, so that substantially all heat of reaction is converted into heat of vaporization, as a heat sink in order to prevent the usual temperature rise in a commercial adiabatic reactor. The hydrogenation is carried out by contacting the $C_4$ cut with hydrogen in the presence of a palladium catalyst on a substantially inert support, having a palladium content in the range of about 0.01 to 1.0 wt.%, preferably 0.01 to 0.1 wt.%. Preferably the catalyst also contains chromium, suitably at concentrations in about the same ranges. The preferred support is alumina. Temperatures of about 50° to about 90° C. are used and pressures sufficient to maintain the hydrocarbons in a mixed vapor-liquid phase.

It is noted that in most laboratory and pilot plant experiments the adiabatic temperature rise is prevented by use of a sandbath or other means to maintain constant temperature but that this cannot be done economically in a commercially sized fixed bed reactor in which a temperature profile is obtained in accordance with the released heat of reaction.

In accordance with this invention, a butene stream containing a substantial amount of butene-1 of at least 30% and containing butadiene as an impurity, viz., 0.05 to 6 wt.% butadiene, and which may contain other impurities that can be hydrogenated, is treated with hydrogen under controlled conditions in combination as discussed above to hydrogenate the butadiene to butene while minimizing losses of butene-1 due to isomerization of butene-1 to butene-2 and hydrogenation of butene to butane.

DESCRIPTION OF THE DRAWING

The attached FIGURE is a graph showing the effect on butadiene conversion of variation in mass velocity of a butene-1 containing feed.

DETAILED DESCRIPTION

The reactions which can occur are illustrated by the following two sets of equations:

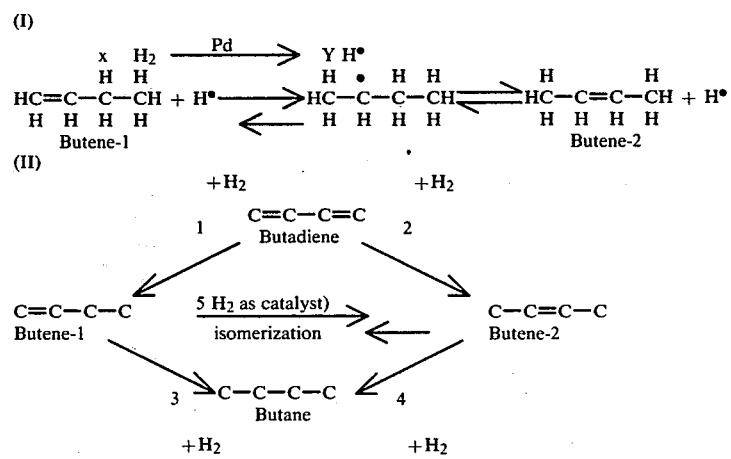

Only reactions 1 and 2 of Set II are wanted.

The observed first order reaction rate of butene-1 disappearance due to isomerization and hydrogenation depends on the various factors discussed herein.

Temperatures above about 90° C. have a very profound effect on butene-1 isomerization, and higher temperatures also on hydrogenation. The temperature may suitably be in the range of 50° to 90° C., preferably 60° to 80° C. to minimize butene-1 loss.

It is the outlet temperature which is responsible for butene-1 loss, therefore temperature rise across the reactor should be minimized and should not exceed about 5°–10° C.

It has further been found that maintaining the hydrocarbon mixture in a mixed vapor-liquid phase contributes greatly to obtaining high selectivity. The selectivity improvement occurs in part through the use of the mass transfer of hydrogen from the vapor to the liquid phase as an effective means to limit the availability of hydrogen per unit time at the active catalyst sites as long as the catalyst surface is wetted as an effective barrier to hydrogen transfer from the gas through the liquid into the catalyst.

In addition to the effects of mixed-phase operation on the distribution of butadiene, butene-1 and hydrogen between liquid and vapor phases and on adsorption phenomena on the catalyst surface, mixed-phase operation directly reduces the reactor outlet temperature. In vapor phase work to remove 0.5–1.5% of residual butadiene, a temperature rise of 60°–100° C. takes place across the catalyst bed. However, in mixed-phase operation at bubble point of the liquid, the heat of reaction is converted into heat of vaporization. A temperature rise of only 3°–5° C. has been observed. This changes the adiabatic reaction to an almost isothermal reaction, reduces reactor outlet temperature significantly, and thereby greatly reduces isomerization and hydrogenation of butene-1.

The preferred operating pressure will therefore fall between about 6 to 15 atmospheres (88 and 220 psia), depending on the operating temperature and the pressure drop across the reactor.

It can thus be seen that the mixed vapor-liquid phase mode cooperates with maintaining the temperature within the reactor in the desired, restricted range and thus in achieving high selectivity.

Hydrogenation of butadiene to butene, hydrogenation of butene to butane, and isomerization of butene-1 to butene-2 are exothermic reactions. The following heats of reaction are reported in the literature.

| Reaction | Heat of Reaction kcal/mol |
|---|---|
| $R-CH=CH_2 \rightarrow R-CH_2-CH_3$ | ca. 30 |
| cis-butene-2→butane | 28.6 |
| trans-butene-2→butane | 27.6 |

Isomerization of butene-1 to butene-2 is slightly exothermic with a heat of isomerization of $\Delta H = 1.4$ to 2.5 kcal/mol.

Assume that 100 mols of butene feed containing 60% of butene-1 and 0.5% of butadiene are hydrofined. The heat of reaction can be calculated as follows:

| Vapor Phase Process | Exothermic Heat of Reaction kcal |
|---|---|
| 0.5 mols $C_4^{==} \times 30$ kcal/mol | 15 |
| 60 mols $C_4^= \times .8$ isomer. (80% isomerization) $\times \sim 2$ kcal/mol | 95 |
| 6 mols $C_4^=$ hydrog. $\times 30$ kcal/mol | 180 |
| Total | 290 |

This 290 kcal/100 mol of feed results in a high temperature rise of 60°–100° C. across the reactor. In contrast, when operating by the present process, a much smaller heat of reaction will occur.

| Present Process | Exothermic Heat of Reaction kcal |
|---|---|
| 0.5 mols $C_4^{==} \times 30$ kcal/mol | 15 |
| 60 mols $C_4^= \times .02$ isom. (2% isomerization) $\times \sim 2$ kcal/mol | 2.4 |
| 0.2 mols $C_4^=$ hydrog. $\times 30$ kcal/mol | 6 |
| Total | 23.4 |

A large reduction in the isomerization significantly affects the heat of reaction and thereby lowers the temperature rise in an adiabatic (commercial) reactor and this reduces a cause of isomerization, namely, higher temperature.

The much smaller heat of reaction will contribute to a much smaller temperature rise as much of it will be absorbed within the reactor by heat of vaporization, i.e., by choosing bubble point temperature/pressure conditions at the reactor inlet.

The rate of isomerization, once it increases slightly as a result of hot spots in the reactor, accelerates due to the temperature sensitivity of the isomerization reaction. This effect is further enhanced by every additional percent of butene which is being hydrogenated to butane at zones of higher reactor temperature.

The mixed phase mode provides an effective heat sink by converting such unscheduled outbursts of heat of reaction into latent heat of vaporization, thereby quenching further self-perpetuating temperature rise and isomerization.

Heat of vaporization for butene at 80° C. is approximately 370 kcal/100 mol, i.e., sufficient to absorb the heat of reaction which, for the cases described above, can vary between 23 and approximately 290 kcal/100 mol.

Useful operating conditions are as follows:

| | |
|---|---|
| Catalyst | 0.01 to 1.0 wt.% Pd, preferably 0.01 to 0.1 wt.% Pd, more preferably 0.03 wt.% Pd on a support; or 0.01 to 1.0 wt.% Pd; 0 to 1.0 wt.% Cr, preferably 0.01 to 0.1 wt.% of each of Pd and Cr, on a support, more preferably 0.03 wt.% Pd, 0.03 wt.% Cr on alumina |
| Hydrogen | 0.1 to 1.0 mol%, preferably 0.1 to 0.9 mol% and more preferably between 0.3 and 0.4 mol% excess on butene-1 over theory |
| Temperature | 50° to 90° C. preferably 60° to 80° C. |
| Temperature Rise Across the Reactor | About 5 to 10° C. or less |
| Pressure | Set for mixed phase, i.e., about 6 to 15 atm. |
| (Liquid) Feed Mass Velocity | Above 1500 lbs/(sq.ft. $\times$ hr) |
| (Liquid) Space Velocity, V/V/H | 1.0–10.0, preferably 2.0 to 3.0 |
| Butadiene Conversion | Above 99.0% to 99.9% |
| Butene-1 Loss | About 2–4% |

The liquid space velocity to be used depends on the activity of the catalyst, i.e., the higher the catalyst activity or the higher the palladium content of the catalyst, the higher the liquid space velocity should be, within the stated range.

The invention is illustrated in the following examples which are not to be taken as limiting.

In each of the following examples the catalyst employed was an alumina-supported Pd-Cr catalyst containing approximately 0.03 wt.% Pd and 0.03 wt.% Cr (unless otherwise indicated). The internal surface area of the catalyst was about 140 m$^2$/g (BET method). All examples were operated with a mixed vapor-liquid phase unless otherwise indicated.

EXAMPLE 1

The feed was a commercial n-butene. An amount of hydrogen was used which exceeded the theoretical amount needed to convert butadiene contained in the feed to n-butene by 50%. The excess amount of hydrogen was 0.45 mol% on butene-1 contained in the feed. The feed and hydrogen mixture was admitted to a packed catalyst bed containing 218 cc (188 g) of catalyst in a reactor tube of ⅓ inch diameter and 16 feet length at constant temperature of 75° C. The reactor outlet pressure was 138 psig. The feed rate was 250 cc/hr. The following results were obtained.

|  | Feed wt.% | Product wt.% |
| --- | --- | --- |
| C$_4$ saturates | 5.6 | 6.0 |
| Butene-1 | 53.8 | 52.7 |
| iso-Butene | 1.8 | 1.8 |
| Butene-2-trans | 22.0 | 22.7 |
| Butene-2-cis | 16.1 | 16.5 |
| Butadiene | 0.4759 | 0.0049 |
| Sulfur | 8 ppm | <1 ppm |
| Butadiene Conversion |  | 99.0% |
| Butene-1 Isomerization |  | 1.5% |
| Butene-1 Hydrogenation |  | 0.5% |
| Total Butene-1 Loss |  | 2.0% |

In this example, the butadiene content was reduced from almost 0.5 wt.% to 49 ppm and sulfur was reduced from 8 ppm to 1 ppm. Thus, high butadiene conversion and simultaneous low butene-1 isomerization were demonstrated.

The above mentioned operating conditions were maintained for 12 days while the amount of hydrogen added was slightly increased from 450 to 600 Scc/hr. The average data of 14 consecutive product analyses gave the following results.

|  | Feed wt.% | Product wt.% |
| --- | --- | --- |
| Butene-1 | 53.8 | 52.7 |
| Butene-2-trans | 22.0 | 22.5 |
| Butene-2-cis | 16.1 | 16.5 |
| Butadiene | 0.4759 | 0.0012 |
| Butadiene Conversion |  | 99.75% |
| Butene-1 Isomerization |  | 1.7% |
| Butene-1 Hydrogenation |  | 0.4% |
| Total Butene-1 Loss |  | 2.1% |

COMPARATIVE EXAMPLE 1a

N-butenes were hydrofined in vapor phase at a pressure of 9 atm. or lower, a reactor inlet temperature of 70° C. and outlet temperature of 150°–190° C., over the same catalyst. The excess amount of hydrogen was 1.5 to 5.0 mol% on butene-1.

Compositions of the feed and product were as follows:

TABLE 1A

|  | Feed wt.% | Product wt.% |
| --- | --- | --- |
| isobutane | 1.2 | 1.2 |

TABLE 1A-continued

|  | Feed wt.% | Product wt.% |
| --- | --- | --- |
| n-butane | 6 | 12 |
| butene-1 | 57 | 28 |
| butene-2 trans | 22 | 36 |
| butene-2 cis | 12 | 23 |
| butadiene-1, 3 | 1.6 | <500 PPM |
| butene-1 loss |  | 50% |

With constant butene-1 content in the feed, the butene-1 concentration in the product was found to vary from 13 to 34% which equals losses in the range of 42 to 76%.

EXAMPLE 2

The feed was made up of a butene-1 butane mixture to which butadiene was added. An amount of hydrogen was used which exceeded the theoretical amount needed to convert the butadiene to n-butene by approximately 100%. The excess hydrogen was 0.9 mol% on butene-1. The feed and hydrogen mixture was admitted to a packed catalyst bed containing 220 cc of catalyst in the apparatus of Example 1 which was held at a constant temperature of 69° C. The reactor outlet pressure was about 135 psig. The feed rate was increased from 220 to 440 cc/hr. The average results of nine product analyses obtained at these conditions during nine days gave a butene-1 loss of 1.7% while butadiene was essentially all converted to n-butene, as shown.

|  | Feed wt.% | Product wt.% |
| --- | --- | --- |
| C$_4$ saturates | 34.8 | 34.8 |
| Butene-1 | 64.2 | 63.1 |
| Butene-2-trans | 0.08 | 1.0 |
| Butene-2-cis | 0.04 | 0.8 |
| Butadiene | 0.71 | <0.001 |
| Butadiene Conversion |  | 99.9% |
| Butene-1 Isomerization |  | 1.7% |
| Butene-1 Hydrogenation |  | 0% |

COMPARATIVE EXAMPLE 2a

A feed rate of 440 cc/hr was used. The temperature was held constant at 69° C. The reactor outlet pressure was 150 psig. The rate of hydrogen was 2700 Scc/hr, equivalent to 28 mol % of butene-1.

The following analytical results were obtained.

|  | Feed wt.% | Product wt.% |
| --- | --- | --- |
| C$_4$ saturates | 34.8 | 35.5 |
| Butene-1 | 64.2 | 61.0 |
| Butene-2-trans | 0.08 | 1.6 |
| Butene-2-cis | 0.04 | 1.5 |
| Butadiene | 0.71 | <0.001 |
| Butene-1 Isomerization |  | 3.9% |
| Butene-1 Hydrogenation |  | 1.1% |
| Total Butene-1 Loss |  | 5.0% |

This example illustrates the need, according to this invention, to limit the hydrogen rate since an increase in hydrogen causes a higher loss of butene-1. In this example butene-1 loss was increased from 1.7% to 5.0%.

COMPARATIVE EXAMPLE 2b

In a laboratory pilot unit, the reactor was maintained at a constant temperature. However, commercially-sized reactors are adiabatic, i.e., heat of reaction increases the reaction temperature across the reactor. Higher temperature further increases butene-1 loss, and the associated hydrogenation and isomerization reactions release additional heat thus self-perpetuating temperature rise and higher butene-1 loss. The effects of higher reaction temperatures of 130° C. and 190° C. are illustrated in the following. The reactor outlet pressure was 160 psig. The feed rate was maintained at 440 cc/hr. The hydrogen rate was 2500 Scc/hr.

|  | Feed wt.% | Product wt.% |  |
| --- | --- | --- | --- |
| Temperature |  | 130° C. | 190° C. |
| $C_4$ saturates | 34.8 | 36.8 | 37.9 |
| Butene-1 | 64.2 | 52.9 | 31.3 |
| Butene-2-trans | 0.08 | 5.8 | 18.1 |
| Butene-2-cis | 0.04 | 4.2 | 12.4 |
| Butadiene | 0.71 | <0.001 | <0.001 |
| Butene-1 Isomerization |  | 15.4% | 47.0% |
| Butene-1 Hydrogenation |  | 3.1% | 4.8% |
| Total Butene-1 Loss |  | 18.5% | 51.8% |

The high butene-1 loss in this comparative example illustrates the need to limit both hydrogen addition and temperature rise in accordance with this invention.

EXAMPLE 3

A more active catalyst containing 0.05% Pd and 0.05% Cr on alumina and having an internal surface of 170 $m^2/g$ (BET method) was used in this example (as well as in 3a and 3b) to illustrate that excess hydrogen must be more limited the more active the catalyst is. The following results were obtained with 220 cc of catalyst in the apparatus of Example 1, a feed rate of 440 cc/hr and a hydrogen rate on 1230 Scc/hr, equivalent to an excess of 0.5 mol% on butene-1. The temperature was maintained constant at 80° C. The reactor outlet pressure was 138 psig.

|  | Feed wt.% | Product wt.% |
| --- | --- | --- |
| $C_4$ saturates | 34.1 | 34.3 |
| Butene-1 | 64.8 | 62.7 |
| Butene-2-trans | 0.07 | 1.7 |
| Butene-2-cis | 0.03 | 1.0 |
| Butadiene-1,3 | 0.8353 | 0.0066 |
| Butadiene Conversion |  | 99.2% |
| Butene-1 Isomerization |  | 2.9% |
| Butene-1 Hydrogenation |  | 0.3% |
| Total Butene-1 Loss |  | 3.2% |

COMPARATIVE EXAMPLE 3a

The liquid feed rate of 440 cc/hr is maintained, but the rate of hydrogen is increased from 1230 Scc/hr to 1800 Scc/hr, equivalent to an excess of 1.3 mol% on butene-1. The temperature is maintained constant at 80° C., pressure is the same.

|  | Feed wt.% | Product wt.% |
| --- | --- | --- |
| $C_4$ saturates | 34.1 | 36.4 |
| Butene-1 | 64.8 | 37.8 |
| Butene-2-trans | 0.07 | 16.1 |
| Butene-2-cis | 0.03 | 9.5 |
| Butadiene-1,3 | 0.8353 | <0.001 |
| Butene-1 Isomerization |  | 38.2% |
| Butene-1 Hydrogenation |  | 3.5% |
| Total Butene-1 Loss |  | 41.7% |

This comparative example illustrates the much larger effect of excess hydrogen on the isomerization of butene-1 when a larger excess of hydrogen is used with a more active catalyst. Hence, the more active the catalyst is, the smaller should be the excess hydrogen used, within the stated range.

COMPARATIVE EXAMPLE 3b

Both excess hydrogen and increase of temperature across the reactor must be limited, the latter directly resulting from too high an excess of hydrogen. In this comparative example a feed rate of 440 cc/hr is maintained, whereas the hydrogen rate is increased from 1200 Scc/hr to 2070 Scc/hr. Simultaneously, the temperature increases from 80° C. to 190° C. The reactor outlet pressure is 140 psig.

|  | Feed wt.% | Product wt.% |  |
| --- | --- | --- | --- |
| Temperature |  | 80° C. | 190° C. |
| $C_4$ saturates | 14.3 | 14.3 | 19.6 |
| Butene-1 | 84.7 | 83.6 | 47.4 |
| Butene-2-trans | 0.10 | 1.1 | 17.4 |
| Butene-2-cis | 0.04 | 0.9 | 15.4 |
| Butadiene | 0.82 | 0.0058 | <0.001 |
| Butene-1 Isomerization |  | 1.3 | 37.7 |
| Butene-1 Hydrogenation |  | 0 | 6.3 |
| Total Butene-1 Loss |  | 1.3 | 44.0 |

EXAMPLE 4

The feed was 99% butene-1 to which butadiene was added. The apparatus was the same as in Example 1. Temperature was 70° C. and pressure was 175 psig. Feed rate was 220 cc/hr. Hydrogen rate was 1000 Scc/hr, equivalent to an excess of 1.0% of butene-1. The results are shown below.

|  | Feed wt.% | Product wt.% |
| --- | --- | --- |
| Butene-1 | 98.6 | 97.6 |
| Butene-2-trans | .26 | 1.22 |
| Butene-2-cis | .16 | .80 |
| Butadiene | .87 | .0079 |
| Butadiene Conversion |  | 99.1% |
| Butene-1 Isomerization Loss |  | 1.0% |

COMPARATIVE EXAMPLE 4a

The hydrogen rate was increased by 50%, from 1000 to 1500 Scc/hr, equivalent to an excess of 1.5 mol% on butene-1. Other conditions remained the same. Isomerization of butene-1 increases as a result of a larger excess of hydrogen as shown in the following table.

|  | Feed wt.% | Product wt.% |
| --- | --- | --- |
| Butene-1 | 98.6 | 95.08 |
| Butene-2-trans | .26 | 2.00 |
| Butene-2-cis | .16 | 1.79 |
| Butadiene | .87 | <0.001 |
| Butadiene Conversion |  | 99.9% |

|  | Feed wt.% | Product wt.% |
|---|---|---|
| Butene-1 Isomerization Loss |  | 3.6% |

In this comparative example, with a 99% butene-1 feed, the increase in the hydrogen addition rate is responsible for the increase of butene-1 loss from 1.0% to 3.6%.

EXAMPLE 5

In a plant scale test n-butenes were hydrofined in a reactor containing 4,900 liters of catalyst. The feed rate was 16,800 liters/hour (equivalent to a mass velocity of 1680 lbs./(sq. ft.×hr.), and the gas rate was 40,000 liters/hour containing 65% of hydrogen. The gas rate is equivalent to an excess amount of hydrogen of 0.37 mols per 100 mols of butene-1 in the feed. The reactor inlet temperature was 85° C. A pressure of 11.0–11.4 atm. was maintained to keep sufficient liquid feed on the catalyst to provide a heat sink for heat of reaction. The results are shown below.

|  | Feed mol% | Product mol% |
|---|---|---|
| C$_4$ saturates | 21.1 | 21.3 |
| Butene-1 | 43.4 | 42.2 |
| iso-Butene | 1.4 | 1.4 |
| Butene-2-trans | 19.2 | 20.3 |
| Butene-2-cis | 12.9 | 13.4 |
| Butadiene | 0.4900 | 0.0360 |
| Butadiene Conversion |  | 92.7% |
| Butene-1 Isomerization |  | 2.4% |
| Butene-1 Hydrogenation |  | 0.4% |
| Total Butene-1 Loss |  | 2.8% |
| Temperature rise across reactor |  | 5.9° C. |

COMPARATIVE EXAMPLE 5a

In vapor phase operation of a n-butene hydrofiner a temperature rise of 60°–100° C. is observed between inlet and outlet temperature of the reactor; the rate of butene-1 isomerization in this vapor phase operation varies between about 20 and 80%. At the same time some 2–5 percent of n-butenes are hydrogenated to butane.

A relatively high rate of isomerization of 20–40% is also obtained when greatly limiting the addition of hydrogen and operating in a liquid phase, i.e., when conditions in combinations as outlined in this invention are not met.

COMPARATIVE EXAMPLE 5b

In this comparative example the reactor pressure was lowered from 11.0 to 9.3 atm., thus vaporizing a greater portion of the feed. The results were a higher temperature rise across the reactor and a large increase in butene-1 isomerization. The feed rate was 16,800 liters/hour and inlet temperature was 85° C.

|  | Feed mol% | Product mol% |
|---|---|---|
| C$_4$ saturates | 20.2 | 20.5 |
| Butene-1 | 44.3 | 33.7 |
| iso-Butene | 1.4 | 1.4 |
| Butene-2-trans | 19.4 | 26.8 |
| Butene-2-cis | 12.9 | 16.6 |
| Butadiene | 0.4900 | 0.0075 |
| Butadiene Conversion |  | 98.5% |
| Butene-1 Isomerization |  | 23.3% |
| Butene-1 Hydrogenation |  | 0.6% |
| Total Butene-1 Loss |  | 23.9% |
| Temperature rise across reactor |  | 10.2° C. |

A very large increase in the loss of butene-1 from 2.8% to 23.9% in this comparative example is caused by a too low reaction pressure. At this lower pressure, a smaller portion of the feed is available as heat sink in the liquid phase, thus allowing the reaction temperature to rise by 10.2° C.

COMPARATIVE EXAMPLE 5c

In order to maintain not only low rates of butene-1 isomerization and hydrogenation but simultaneously to achieve high butadiene conversion, it is necessary, according to this invention, to use a small excess of hydrogen over that theoretically required to convert butadiene to n-butene, to operate at a moderate temperature such as less than 85° C., to avoid an increase of temperature rise across the reactor and to maintain a liquid product on the catalyst sufficient to act as a heat sink. According to this invention, it is necessary to maintain a (liquid) feed mass velocity of more than 1500 lbs/(sq. ft.×hr), preferably more than 2000 lbs/(sq. ft.×hr). The detrimental effect of a lower feed rate on butadiene conversion is illustrated in this comparison in which the feed rate was reduced from 16,800 to 14,200 liters/hr (equivalent to a mass velocity of 1420 lbs/(sq. ft.×hr), and the gas rate was correspondingly reduced to 34,000 liters/hr. The reactor inlet temperature was 85° C., pressure was 11 atm.

|  | Feed mol% | Product mol% |
|---|---|---|
| C$_4$ saturates | 20.2 | 20.3 |
| Butene-1 | 44.9 | 44.3 |
| iso-Butene | 1.4 | 1.4 |
| Butene-2-trans | 20.0 | 20.4 |
| Butene-2-cis | 12.9 | 13.3 |
| Butadiene | 0.5000 | 0.0900 |
| Butadiene Conversion |  | 82.0% |

The low butadiene conversion of 82% versus 92.7% in example 5 is a result of lower throughput, viz., a mass velocity lower than 1500 lbs/(sq. ft.×hr). The effect of mass velocity on butadiene conversion is further illustrated in the attached figure in which butadiene conversions resulting from different feed rates are plotted.

EXAMPLE 6

In a plant scale test, the feed consisted of mixed butenes after butadiene removal but before isobutylene removal; thus the feed contained only 42.2 wt.% butene-1. The hydrogen addition in this test was reduced until essentially all hydrogen was consumed, i.e., no hydrogen was noticeable in the outlet of the reactor. The feedstock contained 1.3 wt.% butadiene. Reactor inlet temperature was 70° C. and temperature rise across the reactor was less than 5° C. Pressure was set at about 10 atm. for mixed vapor-liquid phase conditions.

|  | Feed wt.% | Product wt.% |
|---|---|---|
| Isobutane | 0.4 | 0.5 |
| N-butane | 2.3 | 2.9 |
| Butene-1 | 42.2 | 41.9 |
| iso-Butene | 33.9 | 33.7 |
| Butene-2 trans | 12.3 | 13.2 |
| Butene-2 cis | 7.6 | 7.9 |
| Butadiene | 1.3 | <0.1 |
| Butadiene Conversion |  | >92% |
| Butene-1 Loss |  | 0.7% |

What is claimed is:

1. A process for selectively hydrogenating butadiene present as an impurity in a hydrocarbon feed containing at least 30 wt.% butene-1 while minimizing isomerization of butene-1 to butene-2 which comprises contacting the feed with hydrogen in the presence of a solid catalyst comprising palladium on a support wherein the palladium concentration is in the range of from about 0.01 to about 1.0 weight % at a temperature in the range of about 50° to about 90° C., at a pressure sufficient to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(Sq. ft.×H).

2. A process for selectively hydrogenating butadiene present as an impurity in a $C_4$ hydrocarbon feed containing at least 50 wt.% butene-1 while limiting isomerization of butene-1 to butene-2 to less than 4% which comprises contacting the feed with hydrogen in a reactor in the presence of a solid catalyst comprising palladium and chromium on an alumina support, wherein each of the palladium and chromium is present in the range of from about 0.01 to 0.1 weight %, at a temperature in the range of about 50° to about 90° C. and a pressure in the range of about 6 to 15 atmospheres, the pressure being selected so as to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(Sq. ft.×H).

3. A process as set forth in claim 2 in which the catalyst contains approximately 0.03 weight % palladium and 0.03 weight % chromium.

4. A process as set forth in claim 3 in which the liquid hourly space velocity is in the range of 2 to 3 V/V/H.

5. A process as set forth in claim 2 in which the temperature at the reactor inlet is in the range of about 50° to about 80° C. and the temperature rise across the reactor is not greater than about 10° C.

6. A process as set forth in claim 2 in which the feed contains about 30 to about 75 weight % of butene-1.

7. A process as set forth in claim 6 in which the feed has further been fractionated and contains about 75 to about 99.5 weight % butene-1.

8. A process as set forth in claim 2 in which the feed is a steam cracked fraction which has been treated to extract butadiene and to remove isobutylene substantially.

9. A process as set forth in claim 2 in which the feed contains about 0.05 to 6 weight % butadiene.

10. A proces for selectively hydrogenating butadiene present in a concentration of about 0.5 to 1.0 weight % in a $C_4$ hydrocarbon feed containing at least 50 weight % butene-1 which comprises contacting the feed with hydrogen in a reactor in the presence of a solid catalyst comprising palladium and chromium on an alumina support, wherein each of the palladium and chromium is present in a concentration of approximately 0.03 weight %, maintaining the temperature in the range of about 60° to about 80° C., the pressure being in the range of about 6 to 15 atmospheres and being selected to maintain the hydrocarbon in a mixed liquid-vapor phase, the hydrogen being in a molar excess over theoretical for conversion of the butadiene to butene, of 0.1 to 0.9% based on butene-1, the feed being passed to the catalyst at a mass velocity of more than 1500 lbs./(Sq. ft.×H) to limit isomerization of butene-1 to butene-2 to less than 4%.

* * * * *

REEXAMINATION CERTIFICATE (209th)

United States Patent [19]

Puls et al.

[11] B1 4,260,840

[45] Certificate Issued Jun. 12, 1984

[54] BUTENE-1 CONTAINING FEED PURIFICATION PROCESS (CS-165)

[75] Inventors: Friedrich H. Puls, Baton Rouge, La.; Klaus D. Ruhnke, Pulheim, Fed. Rep. of Germany

[73] Assignee: Exxon Research & Engineering Co., Florham Park, N.J.

Reexamination Request:
No. 90/000,335, Feb. 28, 1983

Reexamination Certificate for:
Patent No.: 4,260,840
Issued: Apr. 7, 1981
Appl. No.: 111,245
Filed: Jan. 11, 1980

[51] Int. Cl.$^3$ .............................................. C07C 5/03
[52] U.S. Cl. .................................... 585/259; 585/261

[56] References Cited

U.S. PATENT DOCUMENTS 3,098,882  7/1963  Arnold ................................. 585/259
3,485,887  12/1969  Kronig et al. ....................... 585/260

FOREIGN PATENT DOCUMENTS 1112729  8/1961  Fed. Rep. of Germany .

OTHER PUBLICATIONS

Lurgi Gesellschaften, "Bayer's Selective Hydrogenation Process", PKH 221-227, Nov. 1976.
Ibid., PKH 231-237.
Y. Furukawa et al., "Study of the Selective Hydrogenation of Butadiene...", (Part 2 and Part 3), Bulletin of the Japan Petroleum Institute, vol. 15, No. 1, May 1973, pp. 64-78.
Ibid., pp. 56-63.
Eleazar et al., "Hydro-isomerization of $C_4$s", Hydrocarbon Processing (I), May 1979, pp. 112-118.
Derrien et al., "Hydrogenate for Pure $C_4$s", Hydrogen Processing (II), May 1979, pp. 175-179.

*Primary Examiner*—Curtis R. Davis

[57] ABSTRACT

The invention concerns selectively hydrogenating butadiene to butene in a $C_4$ fraction containing at least 30 weight % butene-1 by treatment with hydrogen under carefully controlled conditions which comprise in combination use of a supported palladium catalyst containing about 0.01 to about 1.0 weight % palladium, a small excess of hydrogen over theoretical, temperatures in the range of about 50° to about 90° C., pressures sufficient to maintain the hydrocarbons in a mixed vapor-liquid phase and a mass velocity of above 1500 lbs./(Sq. ft.×H).

REEXAMINATION CERTIFICATE ISSUED UNDER 35 U.S.C. 307.

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 6 and 10 are determined to be patentable as amended:

Claims 3–5 and 7–9, dependent on amended claims, are determined to be patentable.

New claims 11–13 are added and determined to be patentable.

1. A process for selectively hydrogenating butadiene present as an impurity in a hydrocarbon feed containing at least 30 wt.% butene-1 *to form a butene-1 rich stream containing not more than 500 ppm butadiene* while [minimizing] *limiting* isomerization of butene-1 to butene-2 to *less than 4%* which comprises contacting the feed with hydrogen in the presence of a solid catalyst comprising palladium on a support wherein the palladium concentration is in the range of from about 0.01 to about 1.0 weight % at a temperature in the range of about 50° to about 90° C., at a pressure sufficient to maintain the hydrocarbons in a mixed liquid-vapor phase, the hydrogen being in a molar excess over theoretical for conversion on the butadiene to butene, of 0.1 to 1.0% based on butene-1, the feed being passed to the catalyst at a mass velocity of more than 1500 lbs./(Sq. ft. × H).

2. A process for selectively hydrogenating butadiene present as an impurity in a C$_4$ hydrocarbon feed containing at least 50 wt.% butene-1 *to form a butene-1 rich stream containing not more than 500 ppm butadiene* while limiting isomerization of butene-1 to butene-2 to less than 4% which comprises contacting the feed with hydrogen in a reactor in the presence of a solid catalyst comprising palladium and chromium on an alumina support, wherein each of the palladium and chromium is present in the range of from about 0.01 to 0.1 weight %, at a temperature in the range of about 50° to about 90° C. and a pressure in the range of about 6 to 15 atmospheres, the pressure being selected so as to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(Sq. ft. × H).

6. A process [as set forth in claim 2 in which the feed contains] *for selectively hydrogenating butadiene present as an impurity in a C$_4$ hydrocarbon feed containing from about 30 to about 75 weight % of butene-1 to form a butene-1 rich stream containing not more than 500 ppm butadiene while limiting isomerization of butene-1 to butene-2 to less than 4% which comprises contacting the feed with hydrogen in a reactor in the presence of a solid catalyst comprising palladium and chromium on an alumina support, wherein each of the palladium and chromium is present in the range of from about 0.01 to 0.1 weight %, at a temperature in the range of about 50° to about 90° C., and a pressure in the range of about 6 to 15 atmospheres, the pressure being selected so as to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(Sq. ft. × H)*.

10. A process for selectively hydrogenating butadiene present in a concentration of about 0.5 to 1.0 weight % in a C$_4$ hydrocarbon feed containing at least 50 weight % butene-1 which comprises contacting the feed with hydrogen in a reactor in the presence of a solid catalyst comprising palladium and chromium on an alumina support, wherein each of the palladium and chromium is present in a concentration of approximately 0.03 weight %, maintaining the temperature in the range of about 60° to about 80° C., the pressure being in the range of about 6 to 15 atmospheres and being selected to maintain the hydrocarbon in a mixed liquid-vapor phase, the hydrogen being in a molar excess over theoretical for conversion of the butadiene to butene, of 0.1 to 0.9% based on butene-1, the feed being passed to the catalyst at a mass velocity of more than 1500 lbs./(Sq. ft. × H) to limit isomerization of butene-1 to butene-2 to less than 5% *and to form a butene-1 rich stream containing not more than 500 ppm butadiene*.

*11. A process for selectively hydrogenating butadiene present as an impurity in a C$_4$ hydrocarbon feed containing at least 30 wt. % butene-1 to form a butene-1 rich stream containing not more than 100 ppm butadiene while limiting isomerization of butene-1 to butene-2 to less than 4% which comprises contacting the feed with hydrogen in a reactor in the presence of a solid catalyst comprising palladium and chromium on an alumina support, wherein each of the palladium and chromium is present in the range of from about 0.01 to 0.1 weight %, at a temperature in the range of about 50° to about 90° C. and a pressure in the range of about 6 to about 15 atmospheres, the pressure being selected so as to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(sq. ft. × H).*

*12. A process for selectively hydrogenating butadiene present in a concentration of about 0.5 to 6.0 weight % in a C$_4$ hydrocarbon feed, comprising a steam cracked fraction which has been treated to extract butadiene and to remove isobutylene substantially and containing at least 50 weight % butene-1, which comprises contacting the feed with hydrogen in a reactor in the presence of a solid catalyst comprising palladium and chromium on an alumina support, wherein each of the palladium and chromium is present in a concentration of approximately 0.03 weight %, maintaining the temperature in the range of about 60° to about 80° C., the pressure being in the range of about 6 to 15 atmospheres and being selected to maintain the hydrocarbon in a mixed liquid-vapor phase, the hydrogen being in a molar excess over theoretical for conversion of the butadiene to butene, of 0.1 to 0.9% based on butene-1, the feed being passed to the catalyst at a mass velocity of more than 1500 lbs./(Sq. ft. × H) and a liquid hourly space velocity in the range of 2 to 3 V/V/H to limit isomerization of butene-1 to butene-2 to less than 5% and to form a desulfurized butene-1 rich stream containing not more than 100 ppm butadiene.*

*13. A process as set forth in claim 12 in which the temperature rise across the reactor is not greater than 10° C.*

* * * * *

REEXAMINATION CERTIFICATE (209th)

United States Patent [19]

Puls et al.

[11] B1 4,260,840

[45] Certificate Issued    Jun. 12, 1984

[54] BUTENE-1 CONTAINING FEED PURIFICATION PROCESS (CS-165)

[75] Inventors: Friedrich H. Puls, Baton Rouge, La.; Klaus D. Ruhnke, Pulheim, Fed. Rep. of Germany

[73] Assignee: Exxon Research & Engineering Co., Florham Park, N.J.

Reexamination Request:
No. 90/000,335, Feb. 28, 1983

Reexamination Certificate for:
Patent No.: 4,260,840
Issued: Apr. 7, 1981
Appl. No.: 111,245
Filed: Jan. 11, 1980

[51] Int. Cl.$^3$ ................................................. C07C 5/03
[52] U.S. Cl. ..................................... 585/259; 585/261

[56] References Cited

U.S. PATENT DOCUMENTS 3,098,882  7/1963  Arnold ............................. 585/259
3,485,887  12/1969  Kronig et al. .................... 585/260

FOREIGN PATENT DOCUMENTS 1112729  8/1961  Fed. Rep. of Germany.

OTHER PUBLICATIONS

Lurgi Gesellschaften, "Bayer's Selective Hydrogenation Process", PKH 221–227, Nov. 1976.
Ibid., PKH 231–237.
Y. Furukawa et al., "Study of the Selective Hydrogenation of Butadiene...", (Part 2 and Part 3), Bulletin of the Japan Petroleum Institute, vol. 15, No. 1, May 1973, pp. 64–78.
Ibid., pp. 56–63.
Eleazar et al., "Hydro-isomerization of $C_4s$", Hydrocarbon Processing (I), May 1979, pp. 112–118.
Derrien et al., "Hydrogenate for Pure $C_4s$", Hydrogen Processing (II), May 1979, pp. 175–179.

*Primary Examiner*—Curtis R. Davis

[57]    ABSTRACT

The invention concerns selectively hydrogenating butadiene to butene in a $C_4$ fraction containing at least 30 weight % butene-1 by treatment with hydrogen under carefully controlled conditions which comprise in combination use of a supported palladium catalyst containing about 0.01 to about 1.0 weight % palladium, a small excess of hydrogen over theoretical, temperatures in the range of about 50° to about 90° C., pressures sufficient to maintain the hydrocarbons in a mixed vapor-liquid phase and a mass velocity of above 1500 lbs./(Sq. ft.×H).

REEXAMINATION CERTIFICATE ISSUED UNDER 35 U.S.C. 307.

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 6 and 10 are determined to be patentable as amended:

Claims 3–5 and 7–9, dependent on amended claims, are determined to be patentable.

New claims 11–13 are added and determined to be patentable.

1. A process for selectively hydrogenating butadiene present as an impurity in a hydrocarbon feed containing at least 30 wt.% butene-1 *to form a butene-1 rich stream containing not more than 500 ppm butadiene* while [minimizing] *limiting* isomerization of butene-1 to butene-2 *to less than 4%* which comprises contacting the feed with hydrogen in the presence of a solid catalyst comprising palladium on a support wherein the palladium concentration is in the range of from about 0.01 to about 1.0 weight % at a temperature in the range of about 50° to about 90° C., at a pressure sufficient to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(Sq. ft.×H).

2. A process for selectively hydrogenating butadiene present as an impurity in a $C_4$ hydrocarbon feed containing at least 50 wt.% butene-1 *to form a butene-1 rich stream containing not more than 500 ppm butadiene* while limiting isomerization of butene-1 to butene-2 to less than 4% which comprises contacting the feed with hydrogen in a reactor in the presence of a solid catalyst comprising palladium and chromium on an alumina support, wherein each of the palladium and chromium is present in the range of from about 0.01 to 0.1 weight %, at a temperature in the range of about 50° to about 90° C. and a pressure in the range of about 6 to 15 atmospheres, the pressure being selected so as to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(Sq. ft.×H).

6. A process [as set forth in claim 2 in which the feed contains] *for selectively hydrogenating butadiene present as an impurity in a $C_4$ hydrocarbon feed containing from* about 30 to about 75 weight % of butene-1 *to form a butene-1 rich stream containing not more than 500 ppm butadiene while limiting isomerization of butene-1 to butene-2 to less than 4% which comprises contacting the feed with hydrogen in a reactor in the presence of a solid catalyst comprising palladium and chromium on an alumina support, wherein each of the palladium and chromium is present in the range of from about 0.01 to 0.1 weight %, at a temperature in the range of about 50° to about 90° C.,* and a pressure in the range of about 6 to 15 atmospheres, the pressure being selected so as to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(Sq. ft.×H).

10. A process for selectively hydrogenating butadiene present in a concentration of about 0.5 to 1.0 weight % in a $C_4$ hydrocarbon feed containing at least 50 weight % butene-1 which comprises contacting the feed with hydrogen in a reactor in the presence of a solid catalyst comprising palladium and chromium on an alumina support, wherein each of the palladium and chromium is present in a concentration of approximately 0.03 weight %, maintaining the temperature in the range of about 60° to about 80° C., the pressure being in the range of about 6 to 15 atmospheres and being selected to maintain the hydrocarbon in a mixed liquid-vapor phase, the hydrogen being in a molar excess over theoretical for conversion of the butadiene to butene, of 0.1 to 0.9% based on butene-1, the feed being passed to the catalyst at a mass velocity of more than 1500 lbs./(Sq. ft.×H) to limit isomerization of butene-1 to butene-2 to less than 5% *and to form a butene-1 rich stream containing not more than 500 ppm butadiene.*

*11. A process for selectively hydrogenating butadiene present as an impurity in a $C_4$ hydrocarbon feed containing at least 30 wt. % butene-1 to form a butene-1 rich stream containing not more than 100 ppm butadiene while limiting isomerization of butene-1 to butene-2 to less than 4% which comprises contacting the feed with hydrogen in a reactor in the presence of a solid catalyst comprising palladium and chromium on an alumina support, wherein each of the palladium and chromium is present in the range of from about 0.01 to 0.1 weight %, at a temperature in the range of about 50° to about 90° C. and a pressure in the range of about 6 to about 15 atmospheres, the pressure being selected so as to maintain the hydrocarbons in a mixed liquid-vapor phase, the hydrogen being in a molar excess over theoretical for conversion of the butadiene to butene, of 0.1 to 1.0% based on butene-1, the feed being passed to the catalyst at a mass velocity of more than 1500 lbs./(sq. ft.×H).*

*12. A process for selectively hydrogenating butadiene present in a concentration of about 0.5 to 6.0 weight % in a $C_4$ hydrocarbon feed, comprising a steam cracked fraction which has been treated to extract butadiene and to remove isobutylene substantially and containing at least 50 weight % butene-1, which comprises contacting the feed with hydrogen in a reactor in the presence of a solid catalyst comprising palladium and chromium on an alumina support, wherein each of the palladium and chromium is present in a concentration of approximately 0.03 weight %, maintaining the temperature in the range of about 60° to about 80° C., the pressure being in the range of about 6 to 15 atmospheres and being selected to maintain the hydrocarbon in a mixed liquid-vapor phase, the hydrogen being in a molar excess over theoretical for conversion of the butadiene to butene, of 0.1 to 0.9% based on butene-1, the feed being passed to the catalyst at a mass velocity of more than 1500 lbs./(Sq. ft.×H) and a liquid hourly space velocity in the range of 2 to 3 V/V/H to limit isomerization of butene-1 to butene-2 to less than 5% and to form a desulfurized butene-1 rich stream containing not more than 100 ppm butadiene.*

*13. A process as set forth in claim 12 in which the temperature rise across the reactor is not greater than 10° C.*

* * * * *